(12) United States Patent
Duley et al.

(10) Patent No.: US 7,972,780 B2
(45) Date of Patent: Jul. 5, 2011

(54) ITPASE GENE POLYMORPHISMS ASSOCIATED WITH ADVERSE DRUG REACTIONS TO AZATHIOPRINE THERAPY

(75) Inventors: John A. Duley, Brisbane (AU); Jeremy D. Sanderson, London (GB); Anthony M. Marinaki, London (GB)

(73) Assignee: Guy's and St. Thomas' NHS Foundation Trust, London (GB)

( * ) Notice: Subject to any disclaimer, the term of this patent is extended or adjusted under 35 U.S.C. 154(b) by 693 days.

(21) Appl. No.: 11/060,972

(22) Filed: Feb. 18, 2005

(65) Prior Publication Data

US 2005/0202483 A1 Sep. 15, 2005

Related U.S. Application Data

(60) Provisional application No. 60/545,849, filed on Feb. 18, 2004.

(51) Int. Cl.
*C12Q 1/68* (2006.01)
*C07H 21/04* (2006.01)
*C12P 19/34* (2006.01)

(52) U.S. Cl. .................... 435/6; 536/24.3; 435/91.2

(58) Field of Classification Search .................... None
See application file for complete search history.

(56) References Cited

OTHER PUBLICATIONS

Sumi et al, Human Genetics (2002) vol. 111, pp. 360-367.*
Gearry et al (Pharmacogenetics (2004) vol. 14, pp. 779-781.*
De Ridder et al, Ailment Pharmacology Therapy (2006) vol. 23, pp. 1137-1141.*
Sumi et al ( Human Genetics (2002) vol. 111, pp. 360-367).*
Kader et al (Journal of Clinical Gastroenterology (2000) pp. 409-413).*
Zelinkova et al ( Clinical Gastroenterology and Hepatology (2006) pp. 44-49).*
von Ashen et al (Clinical Chemistry (2005) vol. 51, pp. 2282-2288).*
Stenmark et al ( Journal of Biological chemistry (2007) vol. 282, pp. 3182-3187).*
Van Dieren et al ( Alimentary Pharmacology & therapeutics (2007) vol. 26, pp. 643-652).*
Palmieri et al (Alimentary Pharmacology & therapeutics (2007) vol. 26, pp. 737-745).*
Hirschhorn et al. (Genetics in Medicine. vol. 4, No. 2, pp. 45-61, Mar. 2002).*
Ioannidis (Nature Genetics, vol. 29, pp. 306-309, Nov. 2001).*
A.M. Marinaki, et al., Mutation in the ITPA Gene Predicts Intolerance to Azathioprine; Nucleosides Nucleotides Nucleic Acids; Oct. 2004; 23(8-9): 1392-7; PMID: 15571265.
Ansari A.; Pharmacogenetic profiling in azathioprine treatment: TPMT, ITPA, and MTHRF polymorphisms and toxicity; GUT; Apr. 2004; p. A105; vol. 53; No. Suppl. 3; Scotland, UK.
Marinaki A.M. et al.; Allele frequency of inosine triphosphate pyrophosphatase gene polymorphisms in a Japanese population; Nucleosides Nudeotides & Nucleic Acids; Oct. 2004; pp. 1399-1401; vol. 23, No. 8-9.
Heller T. et al.; Rapid detection of ITPA 94C>A and IVS2 + 21A>C gene mutations by real-time fluorescence PCR and in vitro demonstration of effect of ITPA IVS2 + 21A>C polymorphism on splicing efficiency; Clinical Chemistry; 2004: pp. 2182-2184; vol. 50, No. 11.
Marsh Sharon et al.; Distribution of ITPA P32T alleles in multiple world populations; Journal of Human Genetics; Oct. 2004; pp. 579-581; vol. 49, No. 10.
Ansari Azhar R. et al.; Mutation in the ITPA gene predicts intolerance to azathiooprine: Digestive Disease Week Abstracts and Itinerary Planner; May 2003; p. 89; vol. 2003.
Marinaki A. et al.; Mutation in the ITPA gne predicts intolerance to azathioprine; GUT; Apr. 2003; p. A13; vol. 52, No. Suppl. 1; Birmingham, England.
Cao Henian et al.; DNA polymorphisms in ITPA including basis of inosine triphosphatase deficiency: Journal of Human Genetics; 2002: pp. 620-622; vol. 47, No. 11.
Duley J.A. et al.; ITPA polymorphism predicts thiopurine intolerance; Journal of Inherited Metabolic Disease; Sep. 2003; p. 129; vol. 26, No. Suppl. 2; Brisbane Australia.
Gearry Richard B. et al.; Lack of association between the ITPA 94C>A polymorphism and adverse effects from azathioprine; Pharmacogenetics; Nov. 2004; pp. 779-781; vol. 14, No. 11.
Allorge D. et al.; ITPA genotyping test does not improve detection of Crohn's disease patients at risk of azathioprine/6-mercaptopurine induced myelosuprression; GUT; Apr. 2005; p. 565; vol. 54, No. 4.
S.Sumi, et al.; Genetic basis of inosine triphosphate pyrophosphohydrolase deficiency; Hum Genet (2002) 111: 360-367; Springer-Verlag 2002.
A. Marinaki, et al.; Adverse drug reactions to azathioprine therapy are associated with polymorphism in the gene encoding inosine triphosphate pyrophosphatase (ITPase); Pharmacogenetics 2004, 14:181-187, vol. 14, No. 3; Lippincott Williams & Wilkins.
A. Marinaki, et al.; Mutation in the ITPA gene predicts intolerance to azathioprine; Nucleosides Nucleotides Nucleic Acids; Oct. 2004; 23 (8-9): 1393-7; PMID: 15571265 (Abstract only).
Stocco, G. "Genetic Polymorphism of Inosine Triphosphate Pyrophosphatase Is a Determinant of Mercaptopurine Metabolism and Toxicity During Treatment for Acute Lymphoblastic Leukemia," Nature Publishing Group, 2009, vol. 85, No. 2, pp. 164-172.
Uchiyama, Kan, "Thiopurine S-methyltransferase and inosine triphosphate pyrophosphohyrolase genes in Japanese patients with inflammatory bowel disease in whom adverse drug reactions were induced by azathioprine/6-mercaptopurine treatment," J. Gastroenterol., 2009, vol. 44, pp. 197-203.

* cited by examiner (Continued)

*Primary Examiner* — Steven C Pohnert
(74) *Attorney, Agent, or Firm* — Kilpatrick Townsend & Stockton LLP

(57) ABSTRACT

The present invention provides methods for predicting a patient's risk of an adverse drug reaction to a thiopurine drug such as AZA or 6-MP by genotyping the patient for a polymorphism in the gene encoding ITPase (ITPA). The present invention also provides methods for predicting a patient's risk of an adverse drug reaction to a thiopurine drug by determining a level of ITPase activity or ITP in a sample from the patient. The present invention further provides methods for optimizing therapeutic efficacy in a patient receiving a thiopurine drug by determining whether the patient should be given an alternative drug based on the presence or absence of a polymorphism in the ITPA gene.

19 Claims, 1 Drawing Sheet

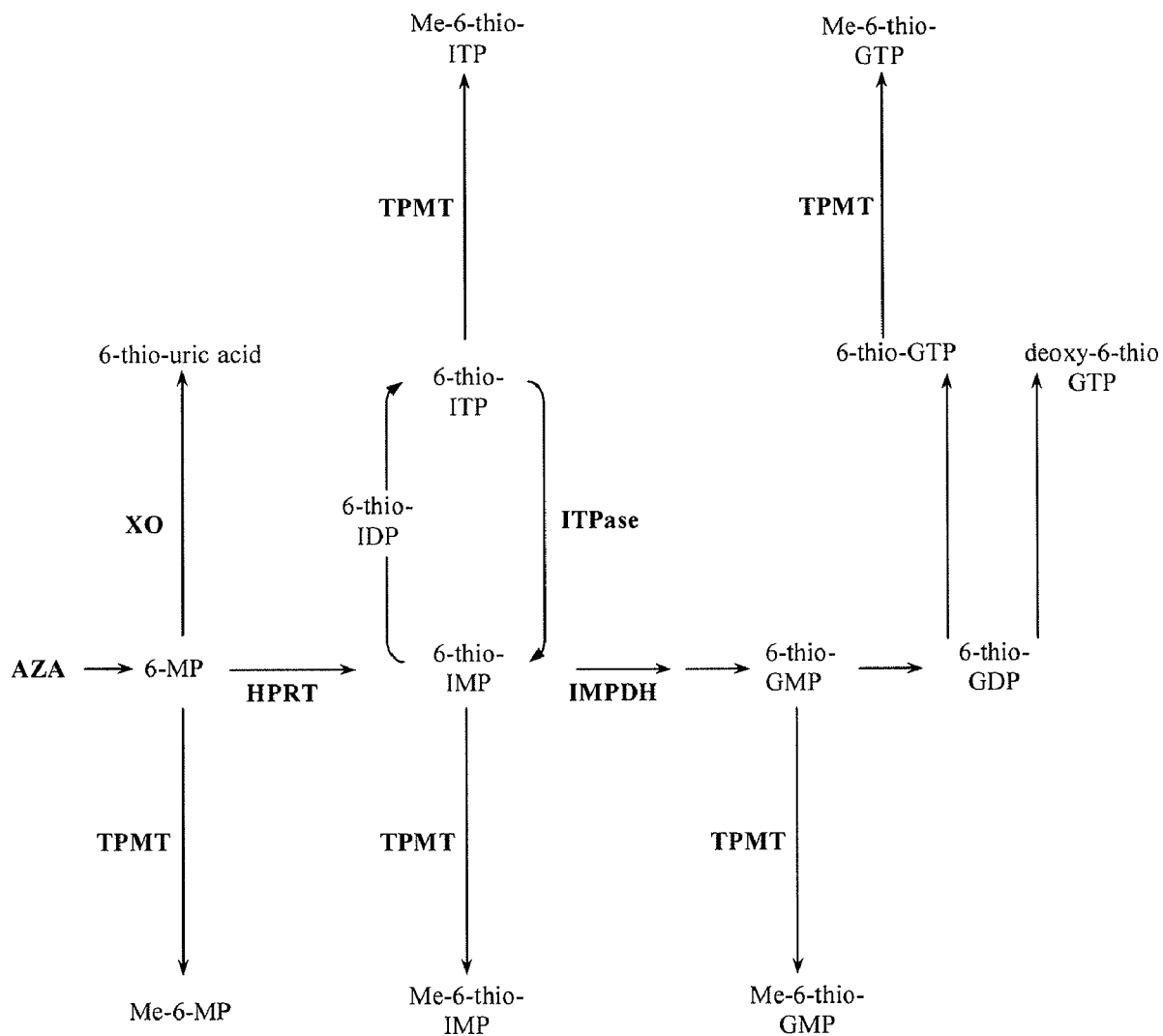

SEQUENCE LISTING

<160> NUMBER OF SEQ ID NOS: 3

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence:ITPA 94C>A
      Forward Primer

<400> SEQUENCE: 1
caggtcgttc agattctagg agaaaagt                                      28

<210> SEQ ID NO 2
<211> LENGTH: 29

```
<212> TYPE: DNA
<213> ORGANISM: Artificial Sequence
<220> FEATURE:
<223> OTHER INFORMATION: Description of Artificial Sequence:IVS2+21A>C
      Forward Primer

<400> SEQUENCE: 2
aaattgaccg tatgtctctg gaatgtttt                                   29

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:Common
      Reverse Primer

<400> SEQUENCE: 3
caagaagagc aagtgtggga caag                                        24
```

ITPASE GENE POLYMORPHISMS ASSOCIATED WITH ADVERSE DRUG REACTIONS TO AZATHIOPRINE THERAPY

CROSS-REFERENCES TO RELATED APPLICATIONS

The present application claims priority to U.S. Provisional Application No. 60/545,849, filed Feb. 18, 2004, which is herein incorporated by reference in its entirety for all purposes.

BACKGROUND OF THE INVENTION

The thiopurine base 6-mercaptopurine (6-MP) and its pro-drug azathioprine (AZA) are widely used in the treatment of chronic inflammatory diseases such as inflammatory bowel disease (IBD), haematological malignancies, and in transplantation. However, adverse drug reactions to AZA or 6-MP occur in 15% to 28% of patients (Schwab et al., *Pharmacogenetics*, 12:429-436 (2002); Lennard, *Gut*, 51:143-146 (2002); Sandborn et al., *Cochrane Database Syst. Rev.*, CD000545 (2000); Ansari et al., *Aliment. Pharmacol. Ther.*, 16:1743-1750 (2002)) and often necessitate withdrawal of therapy.

Genetic polymorphisms in the thiopurine methyltransferase gene (e.g., TPMT*2 to TPMT*8) are associated with deficient TPMT activity (Hon et al., *Hum. Mol. Genet.*, 8:371-376 (1999); Spire-Vayron de la Moureyre et al., *Hum. Mutat.*, 12:177-185 (1998); Otterness et al., *J. Clin. Invest.*, 101:1036-1044 (1998); Otterness et al., *Clin. Pharmacol. Ther.*, 62:60-73 (1997); Krynetski et al., *Proc. Natl. Acad. Sci. USA*, 92:949-953 (1995); Tai et al.,*Am. J. Hum. Genet.*, 58:694-702 (1996)) and the level of TPMT activity has been shown to influence the therapeutic efficacy and toxicity of AZA and 6-MP (Lennard et al., *Ther. Drug Monit.*, 18:328-334 (1996); Lennard et al., *Clin. Pharmacol. Ther.*, 46:149-154 (1989); Lennard, *Ther. Drug Monit.*, 20:527-531 (1998)). For example, a heterozygous TPMT genotype correlates with an increased risk of myelosuppression and other adverse drug reactions (Lennard, *Gut*, 51:143-146 (2002); Ansari et al., *Aliment. Pharmacol. Ther.*, 16:1743-1750 (2002); Dubinsky et al., *Gastroenterology*, 118:705-713 (2000)). Further, patients with a complete TPMT deficiency are at high risk for severe myelosuppression induced by thiopurine therapy (Lennard et al., *Arch. Dis. Child*, 69:577-579 (1993); Lennard et al., *Br. J. Clin. Pharnacol.*, 44:455-461 (1997); Relling et al., *J. Natl. Cancer Inst.*, 91:2001-2008 (1999)). Consistent with the frequency of these alleles in Caucasian populations, adverse drug reactions in only 5 to 10% of patients treated with thiopurine drugs can be explained by the inheritance of one or two TPMT deficiency associated alleles. As a result, in the majority of patients, the pharmacogenetic basis of side-effects is unexplained.

Thus, there is a need to determine the pharmacogenetic basis of adverse drug reactions to AZA or 6-MP in the majority of patients by identifying additional polymorphisms in genes that can be used to predict a patient's tolerance to AZA or 6-MP. Further, there is a need to optimize therapy such as anti-inflammatory or immunosuppressive therapy by determining whether a patient should be given an alternative drug based on the presence or absence of genetic polymorphisms associated with a risk for adverse drug reactions. The present invention satisfies these and other needs.

BRIEF SUMMARY OF THE INVENTION

The present invention is based on the discovery that adverse drug reactions to thiopurine drugs such as AZA and 6-MP are associated with polymorphisms in the gene encoding inosine triphosphate pyrophosphatase (ITPase) or with ITPase enzyme activity. As such, the present invention provides methods for predicting a patient's risk of an adverse drug reaction to a thiopurine drug (e.g., AZA, 6-MP, or metabolites thereof) by genotyping the patient for a polymorphism at the ITPA (ITPase gene) locus. The present invention also provides methods for predicting a patient's risk of an adverse drug reaction to a thiopurine drug by determining a level of ITPase activity or inosine triphosphate (ITP) in a sample from the patient. The present invention further provides methods for optimizing therapeutic efficacy in a patient receiving a thiopurine drug by determining whether the patient should be given an alternative drug based on the presence or absence of a polymorphism in the ITPA gene.

In one aspect, the present invention provides a method for predicting tolerance to a thiopurine drug in a subject, the method comprising:

genotyping the subject at a polymorphic site in the ITPA gene, wherein the presence of a variant allele at the polymorphic site is indicative of the tolerance to the thiopurine drug.

In another aspect, the present invention provides a method for predicting tolerance to a thiopurine drug in a subject, the method comprising:

genotyping the subject for a 94 C to A mutation in the ITPA coding region, wherein the presence of the mutation is indicative of the tolerance to the thiopurine drug.

In yet another aspect, the present invention provides a method for predicting tolerance to a thiopurine drug in a subject, the method comprising:

determining a level of ITPase activity in a sample from the subject, wherein the level of ITPase activity is indicative of the tolerance to the thiopurine drug.

In still yet another aspect, the present invention provides a method for predicting tolerance to a thiopurine drug in a subject, the method comprising:

determining the presence or absence of ITP in a sample from the subject, wherein the presence of ITP is indicative of decreased tolerance to the thiopurine drug.

In a further aspect, the present invention provides a method for optimizing therapeutic efficacy in a subject receiving a thiopurine drug, the method comprising:

genotyping the subject at a polymorphic site in the ITPA gene, wherein the presence of a variant allele at the polymorphic site is indicative of a need to administer an alternative therapeutic agent.

In another aspect, the present invention provides a method for optimizing therapeutic efficacy in a subject receiving a thiopurine drug, the method comprising:

genotyping the subject for a 94 C to A mutation in the ITPA coding region, wherein the presence of the mutation is indicative of a need to administer an alternative therapeutic agent.

One skilled in the art will understand that polymorphic sites in other genes in the thiopurine metabolic pathway can be genotyped in combination with the ITPA gene to predict a patient's risk of an adverse drug reaction to thiopurine drugs such as AZA and 6-MP and to optimize anti-inflammatory or immunosuppressive therapy, e.g., for patients who are AZA-intolerant. Suitable genes include, without limitation, thiopurine methyltransferase (TPMT), IMP dehydrogenase (IMPDH), hypoxanthine phosphoribosyltransferase (HPRT), xanthine oxidase (XO), and combinations thereof.

Other objects, features, and advantages of the present invention will be apparent to one of skill in the art from the following detailed description and figures.

BRIEF DESCRIPTION OF THE DRAWINGS

FIG. 1 shows a metabolic scheme of thiopurine metabolism. 6-Mercaptopurine (6-MP) is salvaged by hypoxanthine phosphoribosyltransferase (HPRT) to form 6-thio-IMP which is further metabolised to form thioguanine nucleotides via IMP dehydrogenase (IMPDH). 6-thio-IMP may also be phosphorylated to form 6-thio-IDP and 6-thio-ITP. Thiopurine inactivation pathways are catalyzed by xanthine oxidase (XO) and TPMT. TPMT is able to add a methyl group (Me-) to 6-MP and thio-nucleotides including 6-thio-ITP and 6-thio-IDP.

DETAILED DESCRIPTION OF THE INVENTION

I. Definitions

As used herein, the following terms have the meanings ascribed to them unless specified otherwise.

The term "thiopurine drug" refers to azathioprine (AZA), 6-mercaptopurine (6-MP), or any metabolite thereof that has therapeutic efficacy and includes, without limitation, 6-thioguanine (6-TG), 6-methylmercaptopurine riboside, 6-thioinosine nucleotides (e.g., 6-thioinosine monophosphate, 6-thioinosine diphosphate, 6-thioinosine triphosphate), 6-thioguanine nucleotides (e.g., 6-thioguanosine monophosphate, 6-thioguanosine diphosphate, 6-thioguanosine triphosphate), 6-thioxanthosine nucleotides (e.g., 6-thioxanthosine monophosphate, 6-thioxanthosine diphosphate, 6-thioxanthosine triphosphate), derivatives thereof, analogues thereof, and combinations thereof.

The term "inflammatory disease" refers to a disease or disorder characterized or caused by inflammation. "Inflammation" refers to a local response to cellular injury that is marked by capillary dilatation, leukocytic infiltration, redness, heat, and pain that serves as a mechanism initiating the elimination of noxious agents and of damaged tissue. The site of inflammation includes the lungs, the pleura, a tendon, a lymph node or gland, the uvula, the vagina, the brain, the spinal cord, nasal and pharyngeal mucous membranes, a muscle, the skin, bone or bony tissue, a joint, the urinary bladder, the retina, the cervix of the uterus, the canthus, the intestinal tract, the vertebrae, the rectum, the anus, a bursa, a follicle, and the like. Such inflammatory diseases include, but are not limited to, inflammatory bowel disease (IBD), rheumatoid arthritis, fibrositis, pelvic inflammatory disease, acne, psoriasis, actinomycosis, dysentery, biliary cirrhosis, Lyme disease, heat rash, Stevens-Johnson syndrome, systemic lupus erythematosus, mumps, autoimmune hepatitis, pemphigus vulgaris, and blastomycosis. Inflammatory bowel diseases are chronic inflammatory diseases of the gastrointestinal tract which include, without limitation, Crohn's disease (CD), ulcerative colitis (UC), and indeterminate colitis. Rheumatoid arthritis is a chronic inflammatory disease primarily of the joints, usually polyarticular, marked by inflammatory changes in the synovial membranes and articular structures and by muscle atrophy and rarefaction of the bones.

The term "haematological malignancy" refers to a group of neoplasms that arise through malignant transformation of bone marrow derived cells. Typical haematological malignancies include, without limitation, acute lymphoblastic leukemia, chronic lymphoid leukemia, diffuse large B-cell lymphoma, follicle center lymphoma, Hodgkin's lymphoma, mantle cell lymphoma, marginal zone lymphoma, Waldenstrom's macroglobulinaemia, myeloma, monoclonal gammopathy of uncertain significance, large granular lymphocyte leukemia, T-prolymphocytic leukemia, Sezary Syndrome, common angio-immunoblastic and anaplastic large cell lymphomas, mycosis fungoides, lymphomatoid papulosis, small intestinal lymphoma, acute myeloid leukemia, myelodysplastic syndrome, myeloproliferative disorders, paroxysmal nocturnal haemoglobinuria, and aplastic anemia.

The term "azathioprine metabolite" refers to any metabolite of azathioprine (AZA) that has therapeutic efficacy and includes, without limitation, 6-mercaptopurine (6-MP), 6-thioguanine (6-TG), 6-methylmercaptopurine riboside, 6-thioinosine nucleotides (e.g., 6-thioinosine monophosphate, 6-thioinosine diphosphate, 6-thioinosine triphosphate), 6-thioguanine nucleotides (e.g., 6-thioguanosine monophosphate, 6-thioguanosine diphosphate, 6-thioguanosine triphosphate), derivatives thereof, and combinations thereof.

The term "therapeutic agent" refers to any composition that can be used to the benefit of a mammalian species, e.g., for treating an inflammatory disease or a haematological malignancy. Such agents may take the form of ions, small organic molecules, peptides, proteins, polypeptides, oligosaccharides, etc. Preferably, the therapeutic agent is an anti-inflammatory agent or an immunosuppressive agent.

The term "anti-inflammatory agent" refers to any substance capable of preventing or reducing inflammation. Suitable anti-inflammatory agents include, without limitation, corticosteroids such as prednisolone, methylprednisolone aceponate, mometasone furoate, hydrocortisone, clobetasol propionate, betamethasone, betamethasone valerate, betamethasone dipropionate, dexamethasone, dexamethasone acetate, fluticasone propionate, clobetasone butyrate, beclomethasone dipropionate, and loteprednol etabonate; non-steroidal anti-inflammatory agents such as diclofenac, diflunisal, etodolac, fenbufen, fenoprofen, flurbiprofen, ibuprofen, indomethacin, ketoprofen, ketorolac, meclofenamate, mefenamic acid, meloxicam, nabumetone, naproxen, nimesulide, oxaprozin, piroxicam, salsalate, sulindac, tolmetin, celecoxib, rofecoxib, and 4-biphenylylacetic acid; antibodies such as infliximab; 5-aminosalicylates such as mesalamine, sulphasalazine, balsalazide, and olsalazine; antibiotics such as clindamycin, erythromycin, tetracycline, minocycline, doxycycline, penicillin, ampicillin, carbenicillin, methicillin, cephalosporins, vancomycin, bacitracin, streptomycin, gentamycin, chloramphenicol, fusidic acid, ciprofloxin and other quinolones, sulfonamides, trimethoprim, dapsone, isoniazid, teicoplanin, avoparcin, synercid, virginiamycin, cefotaxime, ceftriaxone, piperacillin, ticarcillin, cefepime, cefpirome, rifampicin, pyrazinamide, ciprofloxacin, levofloxacin, enrofloxacin, amikacin, netilmycin, imipenem, meropenem, and inezolid; pharmaceutically acceptable salts thereof; derivatives thereof; prodrugs thereof; and combinations thereof.

The term "immunosuppressive agent" refers to any substance capable of producing an immunosuppressive effect, e.g., the prevention or diminution of the immune response, as by irradiation or by administration of drugs such as anti-metabolites, anti-lymphocyte sera, antibodies, etc. Suitable immunosuppressive agents include, without limitation, azathioprine and metabolites thereof such as those described above; anti-metabolites such as methotrexate; immunosuppressive antibodies such as anti-lymphocyte globulin antibodies, anti-thymocyte globulin antibodies, anti-CD3 antibodies, anti-CD4 antibodies, and antibody-toxin conjugates; mizoribine monophosphate; cyclosporine; scoparone; FK-506 (tacrolimus); FK-778; rapamycin (sirolimus); glatiramer acetate; mycopehnolate; pharmaceutically acceptable salts thereof; derivatives thereof; prodrugs thereof; and combinations thereof.

The term "gene" refers to the segment of DNA involved in producing a polypeptide chain; it includes regions preceding and following the coding region, such as the promoter and 3'-untranslated region, respectively, as well as intervening sequences (introns) between individual coding segments (exons).

The term "nucleic acid" or "polynucleotide" refers to deoxyribonucleotides or ribonucleotides and polymers thereof in either single- or double-stranded form including, for example, genomic DNA, cDNA and mRNA. This term encompasses nucleic acid molecules of both natural and synthetic origin as well as molecules of linear, circular, or branched configuration representing either the sense or antisense strand, or both, of a native nucleic acid molecule. It is understood that such nucleic acids can be unpurified, purified, or attached, for example, to a synthetic material such as a bead or column matrix. The term also encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), polymorphisms, alleles, orthologs, SNPs, and complementary sequences as well as the sequence explicitly indicated. The term nucleic acid is used interchangeably with gene, cDNA, and mRNA encoded by a gene.

The term "polymorphism" refers to the occurrence of two or more genetically determined alternative sequences or alleles in a population. A "polymorphic site" refers to the locus at which divergence occurs. Preferred polymorphic sites have at least two alleles, each occurring at a particular frequency in a population. A polymorphic locus may be as small as one base pair (single nucleotide polymorphism, or SNP). Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allele is arbitrarily designated as the reference allele, and other alleles are designated as alternative alleles, "variant alleles," or "variances." The alleles occurring most frequently in a selected population is sometimes referred to as the "wild-type" allele. Diploid organisms may be homozygous or heterozygous for the variant alleles. The variant allele may or may not produce an observable physical or biochemical characteristic ("phenotype") in an individual carrying the variant allele. For example, a variant allele may alter the enzymatic activity of a protein encoded by a gene of interest.

A "single nucleotide polymorphism" or "SNP" occurs at a polymorphic site occupied by a single nucleotide, which is the site of variation between allelic sequences. The site is usually preceded by and followed by highly conserved sequences of the allele (e.g., sequences that vary in less than $\frac{1}{100}$ or $\frac{1}{1000}$ members of the populations). A SNP usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele.

The term "genotype" refers to the genetic composition of an organism, including, for example, whether a diploid organism is heterozygous or homozygous for one or more variant alleles of interest.

The term "sample" refers to any biological specimen obtained from a subject that contains nucleic acid. Suitable samples for use in the present invention include, without limitation, whole blood, plasma, serum, red blood cells, saliva, urine, stool (i.e., feces), tears, any other bodily fluid, tissue samples (e.g., biopsy), and cellular extracts thereof (e.g., red blood cellular extract).

The term "tolerance" refers to the capacity of the body to endure a drug without an adverse drug reaction. The terms "adverse drug reaction" and "side-effect" are used interchangeably herein to refer to an undesirable secondary effect of a drug or therapy. Typical adverse drug reactions include, without limitation, bone marrow suppression, flu-like symptoms, rash, pancreatitis, nausea and vomiting, hepatotoxicity, neutropenia, and combinations thereof.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intraarteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a thiopurine drug such as AZA or 6-MP is administered at the same time, just prior to, or just after the administration of a second drug (e.g., anti-inflammatory agent, immunosuppressive agent, etc.).

II. General Overview

The present invention provides methods for predicting a patient's risk of an adverse drug reaction to a thiopurine drug (e.g., AZA, 6-MP, or metabolites thereof) by genotyping the patient for a polymorphism at the ITPA locus. The present invention also provides methods for predicting a patient's risk of an adverse drug reaction to a thiopurine drug by determining a level of ITPase activity or ITP in a sample from the patient. The present invention further provides methods for optimizing therapeutic efficacy in a patient receiving a thiopurine drug by determining whether the patient should be given an alternative drug based on the presence or absence of a polymorphism in the ITPA gene.

The present invention is based on the discovery that adverse drug reactions to thiopurine drugs such as AZA and 6-MP are associated with a polymorphism in the gene encoding ITPase. More particularly, adverse drug reactions such as flu-like symptoms, rash, and pancreatitis are significantly associated with a polymorphism in ITPA that results in ITPase deficiency, i.e., the 94 C to A mutation. As such, the presence of the 94 C to A mutation or a deficiency in ITPase enzyme activity is indicative of a patient's decreased tolerance for thiopurine drugs such as AZA and 6-MP. Surprisingly, TPMT deficiency only caused nausea and vomiting, and patients with a combination of TPMT and ITPA 94 C to A polymorphisms did not have a substantially altered risk of experiencing an adverse drug reaction. These findings indicate that TPMT deficiency makes a small contribution to overall toxicity while ITPlase deficiency makes a significant contribution. Further, these findings demonstrate the predictive power of determining polymorphisms in ITPA or measuring ITPase enzyme activity levels and the ability to optimize therapeutic efficacy for patients who are ITPase deficient.

III. Description of the Embodiments

In one aspect, the present invention provides a method for predicting tolerance to a thiopurine drug in a subject, the method comprising:

genotyping the subject at a polymorphic site in the ITPA gene, wherein the presence of a variant allele at the polymorphic site is indicative of the tolerance to the thiopurine drug.

In one embodiment, the thiopurine drug is azathioprine (AZA), 6-mercaptopurine (6-MP), or any metabolite thereof. Preferably, the thiopurine drug is AZA, 6-MP, 6-TG, 6-methylmercaptopurine riboside, or combinations thereof. In another embodiment, the subject is receiving the thiopurine drug for the treatment of a disease or disorder such as, for example, a chronic inflammatory disease or a haematological malignancy. Preferably, the subject has rheumatoid arthritis or an inflammatory bowel disease (IBD) such as Crohn'disease (CD), indeterminate colitis, or ulcerative colitis (UC).

In certain instances, a second drug is co-administered with the thiopurine drug. Preferably, the second drug is a drug that enhances the efficacy of the thiopurine drug. As a non-limiting example, a suitable second drug is an anti-inflammatory agent (e.g., infliximab) or an immunosuppressive agent. One skilled in the art will know of other drugs suitable for combination therapy with thiopurine drugs.

In certain instances, the subject is heterozygous for the variant allele in the ITPA gene. In certain other instances, the subject is homozygous for the variant allele in the ITPA gene. In some embodiments, the presence of the variant allele is indicative of decreased ITPase activity, and the reduction in ITPase activity is indicative of 6-thioinosine triphosphate (6-thio-ITP) accumulation. Alternatively, the presence of the variant allele is indicative of increased ITPase activity.

In a preferred embodiment, the variant allele comprises a 94 C to A (94C>A) mutation in the ITPA coding region. In another embodiment, the variant allele comprises a 21 A to C mutation in intron 2 (IVS2+21A>C) of the ITPA gene. In yet another embodiment, the variant allele comprises a 94 C to A mutation in the ITPA coding region and a 21 A to C mutation in intron 2 of the ITPA gene.

In some embodiments, the presence of the variant allele is indicative of decreased tolerance to azathioprine or a metabolite thereof. Typically, the decreased tolerance is associated with an adverse drug reaction such as, for example, bone marrow suppression, flu-like symptoms, rash, pancreatitis, nausea and vomiting, hepatotoxicity, neutropenia, and combinations thereof. Preferably, the decreased tolerance is associated with flu-like symptoms, rash, pancreatitis, or combinations thereof. Alternatively, the presence of the variant allele is indicative of increased tolerance to azathioprine or a metabolite thereof.

In other embodiments, the methods of the present invention further comprise correlating the genotype of the subject with a level of inosine triphosphate pyrophosphatase (ITPase) activity. In certain instances, variant allele homozygosity or heterozygosity at a polymorphic site in the ITPA gene is indicative of deficient (i.e., decreased or absent) ITPase activity. For example, subjects heterozygous for the 94 C to A mutation, heterozygous for the 21 A to C mutation, homozygous for the 21 A to C mutation, or compound heterozygous for both mutations have a decreased level of ITPase activity, whereas subjects homozygous for the 94 C to A mutation have undetectable levels of ITPase activity. In certain other instances, the absence of any variant alleles at the polymorphic site (i.e., a wild-type genotype) is indicative of a normal level of ITPase activity.

In another aspect, the present invention provides a method for predicting tolerance to a thiopurine drug in a subject, the method comprising:

genotyping the subject for a 94 C to A mutation in the ITPA coding region, wherein the presence of the mutation is indicative of the tolerance to the thiopurine drug.

In one embodiment, the thiopurine drug is azathioprine (AZA), 6-mercaptopurine (6-MP), or any metabolite thereof. Preferably, the thiopurine drug is AZA, 6-MP, 6-TG, 6-methylmercaptopurine riboside, or combinations thereof. In another embodiment, the subject is receiving the thiopurine drug for the treatment of any of the above-described diseases or disorders. In certain instances, a second drug such as, for example, an anti-inflammatory agent (e.g., infliximab) or an immunosuppressive agent, is co-administered with the thiopurine drug.

In certain instances, the subject is heterozygous for the 94 C to A mutation in the ITPA gene. In some embodiments, the heterozygous subject has decreased ITPase activity, and the reduction in ITPase activity is indicative of 6-thio-ITP accumulation and decreased tolerance to azathioprine or a metabolite thereof. In certain other instances, the subject is homozygous for the 94 C to A mutation in the ITPA gene. In some embodiments, the homozygous subject has no ITPase activity, and the absence of ITPase activity is indicative of 6-thio-ITP accumulation and decreased tolerance to azathioprine or a metabolite thereof. In yet certain other instances, the subject is compound heterozygous for the 94 C to A mutation and a 21 A to C mutation in intron 2 of the ITPA gene. In some embodiments, the compound heterozygous subject has decreased ITPase activity, and the reduction in ITPase activity is indicative of 6-thio-ITP accumulation and decreased tolerance to azathioprine or a metabolite thereof.

In another embodiment, the presence of the 94 C to A mutation in ITPA is indicative of decreased tolerance to azathioprine or a metabolite thereof. Typically, the decreased tolerance is associated with an adverse drug reaction such as, for example, bone marrow suppression, flu-like symptoms, rash, pancreatitis, nausea and vomiting, hepatotoxicity, neutropenia, and combinations thereof. Preferably, the decreased tolerance is associated with flu-like symptoms, rash, pancreatitis, or combinations thereof.

In a preferred embodiment, the present invention provides a method for predicting tolerance to azathioprine or a metabolite thereof in a subject, the method comprising:

genotyping the subject for a 94 C to A mutation in the ITPA coding region, wherein the presence of the mutation is indicative of decreased tolerance to azathioprine or a metabolite thereof.

In yet another aspect, the present invention provides a method for predicting tolerance to a thiopurine drug in a subject, the method comprising:

determining a level of inosine triphosphate pyrophosphatase (FI?ase) activity in a sample from the subject, wherein the level of ITPase activity is indicative of the tolerance to the thiopurine drug.

In one embodiment, the thiopurine drug is azathioprine (AZA), 6-mercaptopurine (6-MP), or any metabolite thereof. Preferably, the thiopurine drug is AZA, 6-MP, 6-TG, 6-methylmercaptopurine riboside, or combinations thereof. In another embodiment, the subject is receiving the thiopurine drug for the treatment of any of the above-described diseases or disorders. In certain instances, a second drug such as, for example, an anti-inflammatory agent (e.g., infliximab) or an immunosuppressive agent, is co-administered with the thiopurine drug.

The level of ITPase activity in a sample from the subject or a normal control can be measured by any method known to one of skill in the art. As a non-limiting example, ITPase enzyme activity can be measured in saline-washed red blood cells (RBCs) (e.g., stored at −70° C. until ITPase activity is assayed) as described in Duley et al., Clin. Chim. Acta, 188: 243-252 (1990), using an HPLC-based detection method. In certain instances, microfuge tubes (1.5 ml) can contain 150 µl TRIS buffer 100 mmol/L at pH 9.0, 10 µl 10 mmol/L dithiothreitol, 10 µl 1.0 mol/L $MgCl_2$, and 25 µl diluted lysate. After pre-incubation at 37° C. for 5 min, the reaction can be started by the addition of 10 µl 40 mmol/L ITP and then incubated for 15 min at 37° C. The reaction can be stopped by the addition of 25 µl ice-cold 40% trichloroacetic acid (TCA). The TCA can be removed from the deproteinized supernatants by means of water-saturated diethyl-ether. Inosine monophosphate (IMP) can be measured by the HPLC method described above and units (U) of enzyme activity expressed as micromoles IMP formed per hour per gram hemoglobin (Hb). Typically, the level of ITPase activity is about 233±60 U in normal control RBCs; from about 12 to about 185 U in patients heterozygous for the 94 C to A mutation, heterozygous for the 21 A to C mutation, homozygous for the 21 A to C mutation, or compound heterozygous for both mutations; and undetectable (i.e., 0 U) in patients homozygous for the 94 C to A mutation (Sumi et al., *Hum. Genet.*, 111:360-367 (2002)).

In certain instances, a decreased level of ITPase activity relative to a control level is indicative of decreased tolerance to the thiopurine drug. In certain other instances, the absence of ITPase activity is indicative of decreased tolerance to the thiopurine drug. Typically, the decreased tolerance is associated with an adverse drug reaction selected from the group consisting of bone marrow suppression, flu-like symptoms, rash, pancreatitis, nausea and vomiting, hepatotoxicity, neutropenia, and combinations thereof. Preferably, the decreased tolerance is associated with flu-like symptoms, rash, pancreatitis, or combinations thereof.

In some embodiments, the methods of the present invention further comprise correlating the level of inosine triphosphate pyrophosphatase (ITPase) activity to determine the genotype of the subject. In certain instances, deficient (i.e., decreased or absent) ITPase activity is indicative of variant allele homozygosity or heterozygosity at a polymorphic site in the ITPA gene. For example, subjects with a decreased level of ITPase activity are heterozygous for the 94 C to A mutation, heterozygous for the 21 A to C mutation, homozygous for the 21 A to C mutation, or compound heterozygous for both mutations, whereas subjects with undetectable levels of ITPase activity are homozygous for the 94 C to A mutation. In certain other instances, subjects with a normal level of ITPase activity have a wild-type genotype.

In still yet another aspect, the present invention provides a method for predicting tolerance to a thiopurine drug in a subject, the method comprising:

determining the presence or absence of inosine triphosphate (ITP) in a sample from the subject, wherein the presence of IFP is indicative of decreased tolerance to the thiopurine drug.

In one embodiment, the thiopurine drug is azathioprine (AZA), 6-mercaptopurine (6-MP), or any metabolite thereof. Preferably, the thiopurine drug is AZA, 6-MP, 6-TG, 6-methylmercaptopurine riboside, or combinations thereof. In another embodiment, the subject is receiving the thiopurine drug for the treatment of any of the above-described diseases or disorders. In certain instances, a second drug such as, for example, an anti-inflammatory agent (e.g., infliximab) or an immunosuppressive agent, is co-administered with the thiopurine drug.

The presence or absence of ITP in samples from patients and normal controls can be determined by any method known to one of skill in the art, e.g., by measuring the ITP concentration in RBCs. As a non-limiting example, the ITP concentration in RBCs can be measured as described in Simmonds et al., In *Techniques in diagnostic human biochemical genetics: a laboratory manual*, Wiley-Liss, New York, pp 397-424 (1991), using a high pressure liquid chromatography (HPLC) method with a Waters system incorporating an in-line photodiode array and a Phenomenex Hypersil 5 µm amino column (250×3.2 mm). In certain instances, a linear phosphate buffer gradient elution system can be employed at a flow rate of 0.5 ml/min with buffer A (5 mmol/L $KH_2PO_4$, pH 2.5) and buffer B (0.5 mol/L $KH_2PO_4$, 1.0 mol/L KCl, pH 3.5). ITP peaks can be authenticated on the basis of retention time relative to a known standard and the characteristic UV absorbance spectra. ITP concentrations can be quantified from UV absorption at 254 nm. Typically, the ITP concentration is undetectable (i.e., 0 µmol/L) in normal control RBCs; undetectable (i.e., 0 µmol/L) in patients heterozygous for the 94 C to A mutation, heterozygous for the 21 A to C mutation, homozygous for the 21 A to C mutation, or compound heterozygous for both mutations; and from about 88 to about 533 µmol/L in patients homozygous for the 94 C to A mutation (Sumi et al., supra).

Typically, the decreased tolerance is associated with an adverse drug reaction selected from the group consisting of bone marrow suppression, flu-like symptoms, rash, pancreatitis, nausea and vomiting, hepatotoxicity, neutropenia, and combinations thereof. Preferably, the decreased tolerance is associated with flu-like symptoms, rash, pancreatitis, or combinations thereof.

In a further aspect, the present invention provides a method for optimizing therapeutic efficacy in a subject receiving a thiopurine drug, the method comprising:

genotyping the subject at a polymorphic site in the ITPA gene, wherein the presence of a variant allele at the polymorphic site is indicative of a need to administer an alternative therapeutic agent.

In one embodiment, the method further comprises determining the presence of an adverse drug reaction to the thiopurine drug in the subject, wherein the presence of the adverse drug reaction provides further indication of the need to administer an alternative therapeutic agent. For example, the subject can be evaluated for the presence of one or more of the following adverse drug reactions: bone marrow suppression, flu-like symptoms, rash, pancreatitis, nausea and vomiting, hepatotoxicity, and neutropenia. Preferably, the adverse drug reaction evaluated is flu-like symptoms, rash, pancreatitis, or combinations thereof.

In another embodiment, anti-inflammatory therapy or immunosuppressive therapy is optimized. As a non-limiting example, the thiopurine drug can be used for the treatment of any of the above-described diseases or disorders. In certain instances, a second drug, e.g., infliximab, is co-administered with the thiopurine drug.

Suitable alternative therapeutic agents include, without limitation, anti-inflammatory agents, immunosuppressive agents, and combinations thereof. As a non-limiting example, the alternative therapeutic agent can be a 6-MP metabolite such as 6-thioguanine (6-TG) or derivatives thereof. In certain instances, the alternative therapeutic agent is a lower dose of a thiopurine drug. Preferably, the lower dose is between about $\frac{1}{20}$ to about $\frac{1}{2}$ of the normal dose. In certain other instances, the alternative therapeutic agent is a higher dose of a thiopurine drug, e.g., between about twice to about twenty times the normal dose. Preferably, the subject is tolerant to the alternative therapeutic agent.

In a preferred embodiment, the variant allele comprises a 94 C to A mutation in the ITPA coding region. In another embodiment, the variant allele comprises a 21 A to C mutation in intron 2 of the ITPA gene. Typically, the subject is either heterozygous or homozygous for the variant allele, i.e., the presence of one or two copies of the variant allele, respectively. In yet another embodiment, the variant allele comprises a 94 C to A mutation in the ITPA coding region and a 21 A to C mutation in intron 2 of the ITPA gene (i.e., a compound heterozygous genotype). In some embodiments, the presence of the variant allele is indicative of decreased ITPase activity, and the reduction in ITPase activity is indicative of 6-thio-ITP accumulation and decreased tolerance to azathioprine or a metabolite thereof. In other embodiments, the methods of the present invention further comprise correlating the genotype of the subject with a level of inosine triphosphate pyrophosphatase (ITPase) activity.

Therefore, in certain preferred embodiments, alternative therapeutic agents such as 6-TG or a lower dose of AZA or 6-MP can be administered to optimize therapy in subjects having ITPA mutations that cause ITPase deficiencies.

In another aspect, the present invention provides a method for optimizing therapeutic efficacy in a subject receiving a thiopurine drug, the method comprising:

genotyping the subject for a 94 C to A mutation in the ITPA coding region, wherein the presence of the mutation is indicative of a need to administer an alternative therapeutic agent.

In one embodiment, the method further comprises determining the presence of an adverse drug reaction to the thiopurine drug in the subject, wherein the presence of the adverse drug reaction provides further indication of the need to administer an alternative therapeutic agent. For example, the subject can be evaluated for the presence of one or more of the following adverse drug reactions: bone marrow suppression, flu-like symptoms, rash, pancreatitis, nausea and vomiting, hepatotoxicity, and neutropenia. Preferably, the adverse drug reaction evaluated is flu-like symptoms, rash, pancreatitis, or combinations thereof.

In another embodiment, anti-inflammatory therapy or immunosuppressive therapy is optimized. As a non-limiting example, the thiopurine drug can be used for the treatment of any of the above-described diseases or disorders. In certain instances, a second drug, e.g., infliximab, is co-administered with the thiopurine drug.

Suitable alternative therapeutic agents include, without limitation, anti-inflammatory agents, immunosuppressive agents, and combinations thereof. As a non-limiting example, the alternative therapeutic agent can be a 6-MP metabolite such as 6-thioguanine (6-TG) or derivatives thereof. In certain instances, the alternative therapeutic agent is a lower dose of a thiopurine drug. Preferably, the lower dose is between about 1/20 to about 1/2 of the normal dose. In certain other instances, the alternative therapeutic agent is a higher dose of a thiopurine drug, e.g., between about twice to about twenty times the normal dose. Preferably, the subject is tolerant to the alternative therapeutic agent.

In yet another embodiment, the method further comprises genotyping the subject for a 21 A to C mutation in intron 2 of the ITPA gene. Typically, the subject is either heterozygous or homozygous for the variant allele, i.e., the presence of one or two copies of the variant allele, respectively. In a further embodiment, the variant allele comprises a 94 C to A mutation in the ITPA coding region and a 21 A to C mutation in intron 2 of the ITPA gene (i.e., a compound heterozygous genotype). In some embodiments, the presence of the variant allele is indicative of decreased ITPase activity, and the reduction in ITPase activity is indicative of 6-thio-ITP accumulation and decreased tolerance to azathioprine or a metabolite thereof. In other embodiments, the methods of the present invention further comprise correlating the genotype of the subject with a level of inosine triphosphate pyrophosphatase (ITPase) activity.

Therefore, in certain preferred embodiments, alternative therapeutic agents such as 6-TG or a lower dose of AZA or 6-MP can be administered to optimize therapy in subjects having ITPA 94 C to A mutations that cause ITPase deficiencies.

IV. ITPase Deficiency and ITPA Polymorphisms

ITPase deficiency is a clinically benign condition characterized by the marked and abnormal accumulation in erythrocytes of inosine triphosphate (ITP) (Vanderheiden, *Proc. Tenth Congress Int. Soc. Blood Transf.*, Stockholm, 540-548 (1964)). IDP levels are also increased in erythrocytes of ITPase deficient patients (Duley et al., *Clin. Chim. Acta*, 188:243-252 (1990)) by an unknown mechanism. The nucleotide IMP is a central intermediate in purine metabolism and is converted to adenine or guanine nucleotides in nucleated cells. ITP is formed by the phosphorylation of IMP, and in normal cells, ITPase converts ITP back to IMP so that ITP does not accumulate. Deficiency of ITPase interrupts this futile cycle leading to the accumulation ITP. As such, toxicity could result from the accumulation of the metabolite 6-thio-ITP in ITPase-deficient patients treated with thiopurine drugs such as AZA or 6-MP.

ITPase is a widely expressed enzyme (Lin et al., *J. Biol. Chem.*, 276:18695-18701 (2001); Holmes et al., *Clin. Chim. Acta*, 97:143-153 (1979)) and reduced activity has been demonstrated in nucleated cells of patients with ITPase deficiency (Holmes et al., supra). ITPase is a dimeric enzyme with broad substrate specificity (e.g., ITP, dITP, XTP, UTP, dUTP). ITPase is thought to recycle purines trapped in the form of ITP and to protect the cell from the accumulation of nucleotides such as ITP, dITP, and XTP that may be incorporated into RNA or DNA.

The structure of the ITPA gene encoding ITPase has been described and two mutations occurring with polymorphic frequencies that are associated with ITPase deficiency have been identified (Sumi et al., *Hum. Genet.*, 111:360-367 (2002)). Patients homozygous for an open reading frame 94C>A missense mutation (Pro32 to Thr) have zero erythrocyte ITPase activity. Heterozygotes exhibit an ITPase activity that averages 22.5% of the control mean, a level of activity consistent with impaired subunit association of a dimeric enzyme (Lin et al., *J. Biol. Chem.*, 276:18695-18701 (2001)), although the possibility that aberrant splicing resulting from the base substitution cannot be excluded. The ITPA 94C>A polymorphism occurs with a frequency of 0.06 in a U.K. Caucasian population (Sumi et al., id), 0.05 in an African population, and at a higher frequency 0.11 to 0.15 in two Asian populations (Cao et al., *J. Hum. Genet.*, 47:620-622 (2002)). A second polymorphism, IVS2+21A>C, located in intron 2 (Caucasian allele frequency 0.13), has a more subtle effect on ITPase activity, as homozygotes average 60% of the control mean (Sumi et al., supra). Activity in 94C>A/IV2+21A>C compound heterozygotes is 10% of the control mean. In addition, three silent polymorphisms in ITPA (138G>A, 561G>A and 708G>A) have been identified.

V. Variant Alleles

In some embodiments, the methods of the present invention rely on genotyping a subject to detect particular variant alleles, for example, at a polymorphic site in the ITPA gene. As used herein, the term "variant allele" or "variance" means a stably heritable molecular variation that results in altered gene product levels or activity. Thus, a variant ITPA allele is a stably heritable molecular variation that results in altered ITPA levels and/or activity.

Variant alleles useful in the invention include, without limitation, single nucleotide polymorphisms (SNP), microsatellites (ms), variable number tandem repeat (VNTR) polymorphisms, and substitutions, insertions, or deletions of one or more nucleotides. One skilled in the art understands that a variant allele also can be a molecular variation such as abnormal methylation or other modification that does not produce a difference in the primary nucleotide sequence of the variant allele as compared to the wild-type allele.

A variant allele at a polymorphic site in the ITPA gene is located within the ITPA locus, which includes coding regions of the ITPA gene as well as non-coding regions such as introns and 5' and 3' untranslated regions. One skilled in the art understands that such a variant allele can be at a polymorphic site within, for example, a promoter region 5' of ITPA coding sequence, within an enhancer region 5' or 3' of ITPA coding sequence, within an intronic sequence, or within an mRNA stability region 3' of ITPA coding sequence. In one embodiment, the variant allele is located within the ITPA coding sequence (e.g., a 94 C to A mutation in the coding region). In another embodiment, the variant allele is located within an ITPA intronic sequence (e.g., a 21 A to C mutation in intron 2).

In further embodiments, a variant allele at a polymorphic site in the ITPA gene results in decreased ITPA levels and/or enzymatic activity. Homozygosity, heterozygosity, or compound heterozygosity of such ITPA variant alleles can be associated with either tolerance or intolerance to azathioprine therapy. In certain instances, such variant alleles are associated with intolerance to azathioprine therapy as determined, e.g., by the presence of at least one adverse drug reaction to the therapy. In additional embodiments, a variant allele results in increased ITPA levels and/or enzymatic activity.

VI. Methods of Genotyping

A variety of means can be used to genotype a subject at a polymorphic site in the ITPA gene in the methods of the present invention in order to determine whether a sample (e.g., a nucleic acid sample) contains at least one ITPA variant allele. For example, enzymatic amplification of nucleic acid from a subject can be conveniently used to obtain nucleic acid for subsequent analysis. The presence or absence of an ITPA variant allele can also be determined directly from the subject's nucleic acid without enzymatic amplification.

Genotyping of nucleic acid from a subject, whether amplified or not, can be performed using any of various techniques. Useful techniques include, without limitation, polymerase chain reaction (PCR) based analysis, sequence analysis, and electrophoretic analysis, which can be used alone or in combination. As used herein, the term "nucleic acid" means a polynucleotide such as a single- or double-stranded DNA or RNA molecule including, for example, genomic DNA, cDNA and mRNA. This term encompasses nucleic acid molecules of both natural and synthetic origin as well as molecules of linear, circular, or branched configuration representing either the sense or antisense strand, or both, of a native nucleic acid molecule. It is understood that such nucleic acids can be unpurified, purified, or attached, for example, to a synthetic material such as a bead or column matrix.

Material containing nucleic acid is routinely obtained from subjects. Such material is any biological matter from which nucleic acid can be prepared. As non-limiting examples, material can be whole blood, plasma, saliva, cheek swab, or other bodily fluid or tissue that contains nucleic acid. In one embodiment, a method of the present invention is practiced with whole blood, which can be obtained readily by non-invasive means and used to prepare genomic DNA. In another embodiment, genotyping involves amplification of a subject'nucleic acid using the polymerase chain reaction (PCR). Use of PCR for the amplification of nucleic acids is well known in the art (see, e.g., Mullis et al. (Eds.), *The Polymerase Chain Reaction*, Birkhäuser, Boston, (1994)). In yet another embodiment, PCR amplification is performed using one or more fluorescently labeled primers. In a further embodiment, PCR amplification is performed using one or more labeled or unlabeled primers that contain a DNA minor grove binder.

Any of a variety of different primers can be used to amplify a subject's nucleic acid by PCR. For example, the PCR primers disclosed in Example 1 can be used to amplify the ITPA sequence surrounding the 94C>A and/or the IVS2+21A>C polymorphic site. As understood by one skilled in the art, additional primers for PCR analysis can be designed based on the sequence flanking the polymorphic site(s) of interest. As a non-limiting example, a sequence primer can contain from about 15 to about 30 nucleotides of a sequence upstream or downstream of the polymorphic site of interest. Such primers generally are designed to have sufficient guanine and cytosine content to attain a high melting temperature which allows for a stable annealing step in the amplification reaction. Several computer programs, such as Primer Select, are available to aid in the design of PCR primers.

A Taqman® allelic discrimination assay available from Applied Biosystems can be useful for genotyping an individual at a polymorphic site and thereby determining the presence or absence of a variant allele. In a Taqman® allelic discrimination assay, a specific fluorescent dye-labeled probe for each allele is constructed. The probes contain different fluorescent reporter dyes such as FAM and VIC to differentiate amplification of each allele. In addition, each probe has a quencher dye at one end which quenches fluorescence by fluorescence resonance energy transfer. During PCR, each probe anneals specifically to complementary sequences in the nucleic acid from the subject. The 5' nuclease activity of Taq polymerase is used to cleave only probe that hybridizes to the allele. Cleavage separates the reporter dye from the quencher dye, resulting in increased fluorescence by the reporter dye. Thus, the fluorescence signal generated by PCR amplification indicates which alleles are present in the sample. Mismatches between a probe and allele reduce the efficiency of both probe hybridization and cleavage by Taq polymerase, resulting in little to no fluorescent signal. Those skilled in the art understand that improved specificity in allelic discrimination assays can be achieved by conjugating a DNA minor grove binder (MGB) group to a DNA probe as described, e.g., in Kutyavin et al., *Nuc. Acids Research* 28:655-661(2000). Minor grove binders include, but are not limited to, compounds such as dihydrocyclopyrroloindole tripeptide (DPI3).

Sequence analysis can also be useful for genotyping a subject at a polymorphic site. A variant allele can be detected by sequence analysis using the appropriate primers, which are designed based on the sequence flanking the polymorphic site of interest, as is known by those skilled in the art. As a non-limiting example, a sequence primer can contain from about 15 to about 30 nucleotides of a sequence that corresponds to a sequence about 40 to about 400 base pairs upstream or downstream of the polymorphic site of interest. Such primers are generally designed to have sufficient guanine and cytosine content to attain a high melting temperature which allows for a stable annealing step in the sequencing reaction.

The term "sequence analysis" means any manual or automated process by which the order of nucleotides in a nucleic acid is determined. As an example, sequence analysis can be used to determine the nucleotide sequence of a sample of DNA. The term sequence analysis encompasses, without limitation, chemical and enzymatic methods such as dideoxy enzymatic methods including, for example, Maxam-Gilbert and Sanger sequencing as well as variations thereof. The term sequence analysis further encompasses, but is not limited to, capillary array DNA sequencing, which relies on capillary electrophoresis and laser-induced fluorescence detection and can be performed using instruments such as the MegaBACE 1000 or ABI 3700. As additional non-limiting examples, the term sequence analysis encompasses thermal cycle sequencing (Sears et al., *Biotechniques* 13:626-633 (1992)); solid-phase sequencing (Zimmerman et al., *Methods Mol. Cell Biol.* 3:39-42 (1992); and sequencing with mass spectrometry, such as matrix-assisted laser desorption/ionization time-of-flight mass spectrometry (MALDI-TOF MS; Fu et al., *Nature Biotech.* 16:381-384 (1998)). The term sequence analysis further includes, but is not limited to, sequencing by hybridization (SBH), which relies on an array of all possible short oligonucleotides to identify a segment of sequence (Chee et al., *Science* 274:610-614 (1996); Drmanac et al., *Science* 260:1649-1652 (1993); and Drmanac et al., *Nature Biotech.* 16:54-58 (1998)). One skilled in the art understands that these and additional variations are encompassed by the term sequence analysis as defined herein.

Electrophoretic analysis also can be useful in genotyping a subject according to the methods of the present invention. "Electrophoretic analysis" as used herein in reference to one or more nucleic acids such as amplified fragments means a process whereby charged molecules are moved through a stationary medium under the influence of an electric field. Electrophoretic migration separates nucleic acids primarily on the basis of their charge, which is in proportion to their size, with smaller molecules migrating more quickly. The term electrophoretic analysis includes, without limitation, analysis using slab gel electrophoresis, such as agarose or polyacrylamide gel electrophoresis, or capillary electrophoresis. Capillary electrophoretic analysis generally occurs inside a small-diameter (50-100 m) quartz capillary in the presence of high (kilovolt-level) separating voltages with separation times of a few minutes. Using capillary electrophoretic analysis, nucleic acids are conveniently detected by UV absorption or fluorescent labeling, and single-base resolution can be obtained on fragments up to several hundred base pairs. Such methods of electrophoretic analysis, and variations thereof, are well known in the art, as described, for example, in Ausubel et al., *Current Protocols in Molecular Biology* Chapter 2 (Supplement 45) John Wiley & Sons, Inc. New York (1999).

Restriction fragment length polymorphism (RFLP) analysis can also be useful for genotyping a subject at a polymorphic site in the ITPA gene according to the methods of the present invention (Jarcho et al. in Dracopoli et al., *Current Protocols in Human Genetics* pages 2.7.1-2.7.5, John Wiley & Sons, New York; Innis et al.,(Ed.), PCR *Protocols*, San Diego: Academic Press, Inc. (1990)). As used herein, "restriction fragment length polymorphism analysis" refers to any method for distinguishing polymorphic alleles using a restriction enzyme, which is an endonuclease that catalyzes degradation of nucleic acid following recognition of a specific base sequence, generally a palindrome or inverted repeat. One skilled in the art understands that the use of RFLP analysis depends upon an enzyme that can differentiate a variant allele from a wild-type or other allele at a polymorphic site.

In addition, allele-specific oligonucleotide hybridization can be useful for genotyping a subject in the methods of the present invention. Allele-specific oligonucleotide hybridization is based on the use of a labeled oligonucleotide probe having a sequence perfectly complementary, for example, to the sequence encompassing the variant allele. Under appropriate conditions, the variant allele-specific probe hybridizes to a nucleic acid containing the variant allele but does not hybridize to the one or more other alleles, which have one or more nucleotide mismatches as compared to the probe. If desired, a second allele-specific oligonucleotide probe that matches an alternate (e.g., wild-type) allele can also be used. Similarly, the technique of allele-specific oligonucleotide amplification can be used to selectively amplify, for example, a variant allele by using an allele-specific oligonucleotide primer that is perfectly complementary to the nucleotide sequence of the variant allele but which has one or more mismatches as compared to other alleles (Mullis et al., supra). One skilled in the art understands that the one or more nucleotide mismatches that distinguish between the variant allele and other alleles are often located in the center of an allele-specific oligonucleotide primer to be used in the allele-specific oligonucleotide hybridization. In contrast, an allele-specific oligonucleotide primer to be used in PCR amplification generally contains the one or more nucleotide mismatches that distinguish between the variant and other alleles at the 3' end of the primer.

A heteroduplex mobility assay (HMA) is another well-known assay that can be used for genotyping at a polymorphic site in the methods of the present invention. HMA is useful for detecting the presence of a variant allele since a DNA duplex carrying a mismatch has reduced mobility in a polyacrylamide gel compared to the mobility of a perfectly base-paired duplex (Delwart et al., *Science*, 262:1257-1261 (1993); White et al., *Genomics,* 12:301-306 (1992)).

The technique of single strand conformational polymorphism (SSCP) can also be useful for genotyping at a polymorphic site in the methods of the present invention (see, Hayashi, *Methods Applic.,* 1:34-38 (1991)). This technique is used to detect variant alleles based on differences in the secondary structure of single-stranded DNA that produce an altered electrophoretic mobility upon non-denaturing gel electrophoresis. Variant alleles are detected by comparison of the electrophoretic pattern of the test fragment to corresponding standard fragments containing known alleles.

Denaturing gradient gel electrophoresis (DGGE) can be useful in the methods of the present invention. In DGGE, double-stranded DNA is electrophoresed in a gel containing an increasing concentration of denaturant; double-stranded fragments made up of mismatched alleles have segments that melt more rapidly, causing such fragments to migrate differently as compared to perfectly complementary sequences (Sheffield et al., "Identifying DNA Polymorphisms by Denaturing Gradient Gel Electrophoresis" in Innis et al., supra, 1990).

Other molecular methods useful for genotyping a subject at a polymorphic site are known in the art and useful in the methods of the present invention. Such well-known genotyping approaches include, without limitation, automated sequencing and RNAase mismatch techniques (Winter et al., *Proc. Natl. Acad. Sci.,* 82:7575-7579 (1985)). Furthermore, one skilled in the art understands that, where the presence or absence of multiple variant alleles is to be determined, individual variant alleles can be detected by any combination of molecular methods. See, in general, Birren et al. (Eds.) *Genome Analysis: A Laboratory Manual* Volume 1 (Analyzing DNA) New York, Cold Spring Harbor Laboratory Press (1997). In addition, one skilled in the art understands that multiple variant alleles can be detected in individual reactions or in a single reaction (a "multiplex" assay).

In view of the above, one skilled in the art realizes that the methods of the present invention for predicting tolerance or optimizing therapeutic efficacy to a thiopurine drug by genotyping a subject in the ITPA gene can be practiced using one or any combination of the well-known assays described above or other assays known in the art.

VII. EXAMPLES

The following examples are offered to illustrate, but not to limit, the claimed invention.

Example 1

A Mutation in ITPA Predicts Intolerance to Azathioprine Therapy

This example presents a study showing a significant association between the ITPA 94C>A polymorphism and adverse drug reactions to AZA or 6-MP.

Summary

The ITPA 94C>A deficiency-associated allele was significantly associated with adverse drug reactions (odds ratio (OR) 4.2, 95% CI 1.6-11.5, p=0.0034). Significant associations were found for flu-like symptoms (OR 4.7, 95% CI 1.2-18.1, p=0.0308), rash (OR 10.3, 95% CI 4.7-62.9, p=0.0213), and pancreatitis (OR 6.2,CI 1.1-32.6, p=0.0485). Overall, heterozygous TPMT genotypes did not predict adverse drug reactions but were significantly associated with a subgroup of patients experiencing nausea and vomiting as the predominant adverse reaction to AZA therapy (OR 5.5, 95% Cl 1.4-21.3, p=0.0206).

The ITPA 94C>A polymorphism predicts AZA intolerance. Alternative immunosuppressive drugs, particularly 6-thioguanine (6-TG), should be considered for AZA-intolerant patients with ITPase deficiency.

Methods

Patients: Ethical permission for the study was granted by the Ethics Committee of Guy's and St Thomas' NHS Trust. A consecutive series of 89 patients were identified retrospectively from those referred to the Purine Research Laboratory for TPMT phenotyping because of adverse drug reactions experienced on AZA therapy. After restricting the adverse drug reaction cohort to Caucasian patients with IBD and excluding patients in whom necessary clinical information could not be obtained, 62 patients were available for study. Controls were a consecutive series of 68 Caucasian patients attending the IBD clinic at Guy'and St Thomas' Hospitals and treated with AZA for a minimum of 3 months without suffering any adverse drug reaction. The distribution of various features between adverse effect and control groups is shown in Table 1 below. Among these, the only factor differing significantly was dose of AZA received. This is due to the inevitable lower dose received by those developing adverse effects as AZA is mostly initiated at half dose and built up according to tolerance.

TABLE 1

Demographic comparison between control and adverse drug reaction patient groups.

|  | Controls (n = 68) | Adverse drug reactions (n = 62) |
|---|---|---|
| Age in years (mean and range) | 35 (17-82) | 39 (12-78) |
| Sex: Male (%) | 44 | 39 |
| Female (%) | 66 | 61 |
| Diagnosis (%) |  |  |
| Crohns' disease | 74 | 81 |
| Ulcerative colitis | 24 | 19 |
| Indeterminant colitis | 2 | 0 |
| Indication for AZA (%) |  |  |
| Fistula | 9 | 9 |
| Active disease | 0 | 4 |
| Steroid sparing | 91 | 87 |
| AZA dose in mg/kg (median and range) | 1.92* (0.91-3.26) | 1.81* (0.39-2.59) |
| Patients on other drugs (n) |  |  |
| 5-ASA | 38 | 33 |
| Prednisilone | 2 | 7 |
| Cyclosporin | 1 | 0 |

*p = 0.044, two sided Mann-Whitney Rank Sum Test.
5-ASA, 5-aminosalicylic acid.

Hepatotoxicity was defined by serum alanine transaminase levels greater than twice the upper normal limit (50 IU/l) and resolution after withdrawal of AZA; pancreatitis by severe abdominal pain and serum amylase >800 IU/l; neutropenia by a neutrophil count of <2.0×10$^9$ cells. Sixteen patients with flu-like symptoms included 5 patients with myalgia as a prominent symptom. Patients experiencing headaches or severe abdominal pain with normal amylase were grouped as "other".

Laboratory Methods: All patients were genotyped for ITPA 94C>A and IVS2+21A>C mutations. DNA from controls and the adverse drug reaction cohort was extracted from blood samples using a QIAamp DNA blood kit (Qiagen; Crawley, UK). The ITPase 94C>A and IVS2+21A>C polymorphisms were amplified from genomic DNA using mutation specific mismatched forward primers and a common reverse primer in a single multiplexed PCR reaction. DNA was amplified using HotstarTaq DNA Polymerase (Qiagen; Crawley, UK) in a total volume of 20 µl, containing 0.5 µM each of the ITPA 94C>A Forward Primer 5'-CAG GTC GTT CAG ATT CTA GGA GAA AAG T-3' (SEQ ID NO:1), the IVS2+21A>C Forward Primer 5'-AAA TTG ACC GTA TGT CTC TGGAAT GTT TT-3'(SEQ ID NO:2), and a Common Reverse Primer 5'-CAA GAA GAG CAA GTG TGG GAC AAG-3' (SEQ ID NO:3), in a reaction supplemented with 5% DMSO. The thermocycler profile was 35 cycles of 94° C./30 s, 50° C./30 s, and 72° C./30 s. The amplified PCR products were desalted by microdialysis on Millipore Type VS filters (Millipore; UK), digested overnight at 37° C. with XmnI (New England Biolabs; Hitchin, UK) in a buffer supplied by the manufacturer. The 94A>C mutation destroys an XmnI and is seen as an undigested amplicon of 256 bp. Digestion of the wild-type yields fragments of 228 and 28 bp. The IV2+21A>C mutation creates an XmnI site, which leads to restriction fragments of 175 and 29 bp. The wild-type allele is not digested and is seen as a fragment of 204 bp. RFLPs were resolved on 2.5% Agarose-1000 gels (Invitrogen; Paisley, UK). TPMT *3A, *3C, and *2 variants were detected as previously described (Ansari et al., *Aliment. Pharmacol. Ther.*, 16:1743-1750 (2002)). Patients were also phenotyped for erythrocyte TPMT activity as previously described (Ansari et al., supra).

Statistical Methods: Association between adverse drug reaction and polymorphisms in each gene was tested using a two-sided Fisher's exact test; odds ratios (OR) and 95% confidence intervals (CI) were calculated from contingency tables.

Results

The median AZA dose received by the adverse drug reaction group (1.81 mg/kg) was significantly lower than controls (1.92 mg/kg, p=0.044, two-sided Mann-Whitney Rank Sum Test) consistent with a strategy of dose escalation in AZA precription. Median erythrocyte TPMT activity in the control cohort (10.7, range 5.4 to 22.0 U) and patients with side effects (10.6, range 4.9 to 17.1 U) were not significantly different (p=0.159, two-sided Mann-Whitney Rank Sum Test), although the median TPMT activity of 9.7 U found in patients presenting with nausea and vomiting was significantly lower than the control median (p=0.003, two-sided Mann-Whitney Rank Sum Test).

Allele frequencies for TPMT and ITPA deficiency-associated alleles are shown in Table 2 below. TPMT*3A and TPMT*3C alleles were found in the heterozygous state and no TPMT*2 alleles were found. The allele frequencies of the ITPA 94C>A polymorphism in the adverse drug reaction group was elevated (0.17) compared to controls (0.04). By contrast, the ITPA IVS2+21A>C polymorphism in the side-effect cohort was lower (0.08) than in controls (0.12), consistent with the observation that the two polymorphisms do not occur in cis (Sumi et al., *Hum. Genet.*, 111:360-367 (2002)).

TABLE 2

ITPA and TPMT allele frequencies in controls and patients with adverse drug reactions (ADR) to azathioprine.

|  | Controls (n = 68) | ADR (n = 62) |
|---|---|---|
| TPMT*3A | 0.05 | 0.06 |
| TPMT*3C | 0 | 0.02 |
| ITPA 94C > A | 0.04 | 0.17 |
| ITPA IVS2 + 21A > C | 0.12 | 0.08 |

Although a heterozygous TPMT genotype was not significantly associated with thiopurine toxicity overall, a heterozygous TPMT genotype was predictive of nausea and vomiting (see, Table 3 below; OR 5.5 95% CI 1.4-21.3, p=0.0206). The increased frequency of variant TPMT alleles in this group is thus consistent with the significantly lower mean TPMT activity found in this group.

By contrast, there was a significant association between adverse drug reactions to AZA therapy and the ITPA 94C>A allele (see, Table 3 below; OR 4.2 95% CI 1.6-11.5, p=0.0034). Flu-like symptoms (OR 4.7 95% CI 1.2-18.1, p=O.0308), rash (OR 10.3 95% CI 4.7-62.9, p=0.0213), and pancreatitis (OR 6.2 95% CI 1.1-32.6, p=0.0485) were all significantly associated with the ITPA 94C>A mutation. However, the ITPA IVS2+21A>C allele was not predictive of toxicity.

TABLE 3

Association of adverse drug reactions with a TPMT or ITPA variant genotype in patients treated with azathioprine.

|  |  | TPMT *3A + C | ITPA 94C > A | ITPA IVS2 + 21A > C |
|---|---|---|---|---|
| All side effects (n = 62) | Odds ratio | 1.7 | 4.2 | 0.7 |
|  | p-value | p = 0.4360 | p = 0.0034 | p = 0.6403 |
|  | Heterozygotes (n) | 10 | 15 | 8 |
|  | Homozygotes (n) | 0 | 3 | 1 |
| Flu-like symptoms (n = 16) | Odds ratio | 0.3 | 4.7 | 1.0 |
|  | p-value | p = 0.3372 | p = 0.0308 | p = 1.0000 |
|  | Heterozygotes (n) | 0 | 4 | 3 |
|  | Homozygotes (n) | 0 | 1 | 0 |
| Rash (n = 6) | Odds ratio | 4.4 | 10.3 | 0.9 |
|  | p-value | p = 0.1528 | p = 0.0213 | p = 1.0000 |
|  | Heterozygotes (n) | 2 | 3 | 0 |
|  | Homozygotes (n) | 0 | 0 | 1 |
| Pancreatitis (n = 8) | Odds ratio | 1.3 | 6.2 | 0.6 |
|  | p-value | p = 1.0000 | p = 0.0485 | p = 1.0000 |
|  | Heterozygotes (n) | 1 | 3 | 1 |
|  | Homozygotes (n) | 0 | 0 | 0 |
| Nausea and vomiting (n = 13) | Odds ratio | 5.5 | 3.1 | 0.4 |
|  | p-value | p = 0.0206 | p = 0.1529 | 0.4480 |
|  | Heterozygotes (n) | 5 | 1 | 1 |
|  | Homozygotes (n) | 0 | 2 | 0 |
| Hepatotoxicity (n = 4) | Odds ratio | 2.9 | 10.3 | 0.5 |
|  | p-value | p = 0.3824 | p = 0.0584 | p = 1.0000 |
|  | Heterozygotes (n) | 1 | 2 | 0 |
|  | Homozygotes (n) | 0 | 0 | 0 |
| Other (n = 4) | Odds ratio | 0.9 | 3.4 | 4.2 |
|  | p-value | p = 1.0000 | p = 0.3419 | p = 0.1894 |
|  | Heterozygotes (n) | 0 | 1 | 2 |
|  | Homozygotes (n) | 0 | 0 | 0 |
| Neutropenia (n = 11) | Odds ratio | 0.9 | 1.0 | 0.4 |
|  | p-value | p = 1.0000 | p = 1.0000 | p = 0.6781 |
|  | Heterozygotes (n) | 1 | 1 | 1 |
|  | Homozygotes (n) | 0 | 0 | 0 |
| Controls (n = 68) | Heterozygotes (n) | 7 | 6 | 10 |
|  | Homozygotes (n) | 0 | 0 | 3 | p-value for testing against controls, using Fisher's exact test. p < 0.05 considered statistically significant.

Combining TPMT and ITPA 94C>A genotypes did not substantially alter the risk of experiencing an adverse drug reaction (OR 3.5, 95% CI 1.6-7.6, p=0.0023). Excluding TPMT heterozygous genotypes from the side-effect cohort strengthened the association between adverse drug reactions and the ITPA 94C>A polymorphism (OR 5.3, 95% CI 1.9-14.6, p=0.0010). The association between ITPA 94C>A and rash (OR 15.5, 95% CI 2.2-111.8, p=0.0118), and pancreatitis (OR 7.8, 95% CI 1.4-43.1, p=0.0335) increased and the association with nausea and vomiting became significant (OR 6.2, 95% CI 1.2-32.6, p=0.0485).

AZA therapy could be continued at full dose in only 5 of the 62 patients suffering adverse drug reactions. Twenty one patients were re-challenged with a reduced AZA dose. Of the 4 patients heterozygous for a variant TPMT allele, two patients remained intolerant.

Discussion

As shown in Table 3 above, a significant association exists between AZA-related adverse drug reactions and the ITPA 94C>A polymorphism. The majority of patients with ITPA 94C>A alleles were heterozygous, a genotype associated with 25% residual red cell ITPase activity (Sumi et al., *Hum. Genet.*, 111:360-367 (2002)). By contrast, ITPA IVS2+21A>C genotypes were not associated with adverse drug reactions. Carriers of the ITPA IVS2+21A>C polymorphism have ITPase activity in the normal range and homozygotes have about 60% residual activity. Only one of the four ITPA IVS2+21A>C homozygotes was in the adverse drug reaction cohort, suggesting that this level of ITPase activity is sufficient to prevent the accumulation of toxic thiopurine metabolites.

Impaired methylation (and hence inactivation) of 6-MP due to TPMT deficiency leads to enhanced anabolism of the thiopurine base to the active triphosphate 6-thio-(d)GTP (FIG. 1). Toxicity results from a metabolic "overdosing" effect. However, the present study provides an additional mechanism of toxicity whereby the accumulation of a toxic metabolite (i.e., 6-thio-ITP) results from an inherited deficiency of ITPase. As ITP can readily substitute for GTP in many GTP-requiring reactions, the recent report that the immunosuppressive effect of thiopurine drugs is mediated by specific inhibition of Rac1 activation by 6-thio-GTP binding instead of GTP (Tiede et al., *J. Clin. Invest.*, 111: 1133-1145 (2003)) is thus particularly interesting. This mechanism raises the possibilities that, first, the metabolite 6-thio-ITP may contribute to the immunosuppressive properties of 6-MP and, second, that increased levels of 6-thio-ITP likely to be found in ITPase deficiency could precipitate toxicity by binding to Rac1. Alternatively, 6-thio-FFP may inhibit unknown GTP-mediated cell signaling pathways, resulting in toxicity.

Toxicity related to TPMT deficiency provides a classic pharmacogenetic model. However, as demonstrated in this study, TPMT deficiency makes a small contribution to overall toxicity. Neutropenia is the most feared consequence (Lennard, *Gut*, 51:143-146 (2002)), but TPMT deficiency also appears specifically associated with nausea. TPMT or ITPA variant genotypes were found in 45% of patients with adverse drug reactions. As such, other mechanisms may underlie the remainder of the adverse events seen on azathioprine therapy. Some are likely to be cases of straightforward gastric intolerance and others more typical of immunological hypersensitivity. Hepatoxicity, which was not associated with TPMT or ITPase deficiency, may relate to very high TPMT activity, leading to the accumulation of methylated metabolites (Dubinsky et al., *Gastroenterology*, 118:705-713 (2000)). Unknown mutations in the TPMT or ITPA genes, drug-drug interactions (Lennard, *Gut*, 51:143-146 (2002)), and/or sensitivity to the imidazole moiety of AZA (McGovern et al., *Gastroenterology*, 122:838-839 (2002)) are other explanations for intolerance to AZA.

The flu-like illness, often with intense myalgia, seen in the first two weeks of initiating AZA is variable, but may be severe. To date, it has been assumed that this adverse reaction is a result of a TPMT-independent hypersensitivity phenomenon (Schwab et al., *Pharmacogenetics*, 12:429-436 (2002)). However, the results from the present study indicate that it may be attributable to the accumulation of toxic thio-inosine metabolites in individuals with ITPase deficiency. The ITPA 94C>A polymorphism was also significantly associated with pancreatitis and a small number of cases of drug-induced rash. Pancreatitis on AZA has no specific features that differ from other types of drug-induced pancreatitis, appears to be independent of AZA dose and, unlike hepatotoxicity, does not correlate with increased levels of methylated intermediates (Schwab et al., *Pharmacogenetics*, 12:429-436 (2002)).

Most current analytical methods for therapeutic drug monitoring hydrolyze thiopurine nucleotides to the base (Shipkova et al., *Clin. Chem.*, 49(2):260-268 (2003)). The association between ITPase deficiency and adverse drug reactions indicates that the distribution of thiopurine triphosphate nucleotides between guanine and inosine nucleotides may also be important in predicting AZA toxicity. As such, the levels of these thiopurine nucleotides and their methylated derivatives generated by TPMT activity can be used for predicting a clinical outcome to AZA or 6-MP therapy.

Overall, the control and adverse effect groups were comparable in demographic characteristics and concomitant medications, so it seems unlikely therefore that the higher than expected frequency of ITPase deficient individuals in the adverse effect group has occurred as a result of sample bias and the retrospective study design.

In the present study, 3 of 6 patients with ITPA 94C>A alleles tolerated a reduced AZA dose, a proportion similar to the number of TPMT heterozygotes tolerating AZA re-challenge at a reduced dose. As such, AZA therapy can be optimized by adjusting the AZA dose in patients with at least one ITPA 94C>A allele. Further, alternative therapies for ITPase-deficient patients that are ITPA 94C>A heterozygotes or homozygotes, such as 6-thioguanine therapy, can also be considered. As 6-thioguanine is activated directly to the 6-thio-GMP intermediate, 6-thio-IMP would be bypassed and hence 6-thio-ITP would not accumulate in ITPase-deficient patients. Indeed, thioguanine has been used successfully in patients with 6-MP/AZA-related toxicity (Dubinsky et al., *Inflamm. Bowel Dis.*, 7:181-189 (2001)).

Example 2

The ITPA 94C>A Mutation is Associated with Adverse Drug Reactions to Azathioprine Therapy This example presents an additional study showing a significant association between the ITPA 94C>A polymorphism and adverse drug reactions to AZA or 6-MP.

The ITPA genotype, TPMT phenotype, and TPMT genotype in 64 IBD patients with adverse drug reactions to AZA therapy were compared to 71 patients who did not experience side-effects to therapy. Odds ratios (ORs) were calculated using a dominant model.

Overall, the ITPA 94C>A polymorphism was significantly associated with adverse drug reactions to AZA therapy (OR 4.239, CI 1.562-11.504, p=0.0033). Variant TPMT genotypes were not significantly associated with adverse drug reactions but did predict side-effects in a subset of 14 patients having nausea and vomiting (OR 5.079, CI 1.325-19.465, p=0.0239). By contrast, the ITPA 94C>A polymorphism was significantly associated with flu-like symptoms in 11 patients (OR 6.190, CI 1.400-27.371, p=0.0251) and rash in 6 patients (OR 10.833, CI 1.780-65.938, p=O.0190). Myelosuppression, pancreatitis, and hepatitis were not predicted by ITPA or TPMT genotype.

Thus, the ITPA 94C>A mutation predicts intolerance to AZA and is particularly associated with flu-like and rash adverse effects. Immunosuppressive therapy in these AZA-intolerant, ITPase-deficient patients can be optimized by either reducing the dose of AZA or using an alternative drug such as 6-thioguanine.

Example 3

Allele Frequency of ITPA Polymorphisms in a Japanese Population

This example shows the allele frequency of ITPA polymorphisms in a Japanese sample as compared to a Caucasian sample and other ethnic groups.

Summary

The frequencies of ITPA polymorphisms in 100 healthy Japanese individuals were examined. The allele frequency of the ITPA 94C>A variant in the Japanese sample was 0.135 (Caucasian allele frequency 0.060). The ITPA IV2+21A>C polymorphism was not found in the Japanese sample (Caucasian allele frequency 0.130). Allele frequencies of the ITPA 138G>A, 561G>A, and 708G>A polymorphisms were 0.57, 0.18, and 0.06, respectively in the Japanese population, and with the exception of the 138G>A polymorphism, similar to allele frequencies in Caucasians.

Methods

DNA was extracted from blood samples of 100 normal Japanese individuals after informed consent had been obtained. The 5 SNPs in the ITPA gene were determined using PCR-RFLP methods as previously described (Sumi et al., *Hum. Genet.*, 111:360-367 (2002)).

Results

As shown in Table 4, the allele frequency of the ITPA 94C>A mutation in the Japanese sample was 0.135, twice the frequency found in Caucasians (0.060). The ITPA IV2+ 21A>C variant was not found in the Japanese sample, although it occurred with a frequency of 0.130 in Caucasians. Allele frequencies of the ITPA 138G>A, 561G>A and 708G>A polymorphisms were 0.57, 0.18, and 0.06, respectively, in the Japanese population, and with the exception of the 138G>A polymorphism, similar to allele frequencies in Caucasians.

TABLE 4

Frequencies of ITPA alleles associated with reduced ITPase activity in healthy individuals of different ethnic groups.

| | 94C > A | IV2 + 21A > C |
|---|---|---|
| Present study | | |
| Japanese (n = 200) | 0.135* | 0* |
| Caucasian (n = 200) | 0.060 | 0.130 |
| Cao et al. | | |
| Caucasian (n = 250) | 0.07 | not examined |
| African (n = 120) | 0.05 | not examined |
| Chinese (n = 120) | 0.15 | not examined |
| East India (n = 120) | 0.11 | not examined |

Cao et al., J. Hum. Genet., 47:620-622 (2002).
*Significantly different from Caucasians (p < 0.05).

This study shows that ITPase deficiency fulfills the criteria for a locus important in inter-individual differences in purine drug analogue metabolism, namely, it is a benign condition occurring with polymorphic frequencies in most populations and the enzyme has a broad substrate specificity for both purine and pyrimidine triphosphates. As such, a deficiency of the ITPase enzyme due to a ITPA 94C>A mutation is useful in predicting the tolerance of a patient to a thiopurine drug such as AZA or 6-MP, as reduced ITPase activity leads to the accumulation of the 6-thio-IIP and results in adverse drug reactions.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for predicting tolerance to azathioprine (AZA) or 6-mercaptopurine (6-MP) in a human subject having Crohn's disease or ulcerative colitis, said method comprising:
   (a) genotyping nucleic acid in a sample from said subject for the presence of a 94 C to A mutation in the inosine triphosphate pyrophosphatase (ITPA) coding region;
   (b) indicating that the presence of said mutation is predictive of decreased tolerance to AZA or 6-MP; and
   (c) predicting the subject with said mutation has increased risk of flu-like symptoms relative to a subject without said mutation and predicting the subject with said mutation does not have increased risk of myelosuppression relative to a subject without said mutation.

2. The method of claim 1, wherein said subject is heterozygous for said 94 C to A mutation.

3. The method of claim 1, wherein said subject is homozygous for said 94 C to A mutation.

4. The method of claim 1, wherein said subject is compound heterozygous for said 94 C to A mutation and a 21 A to C mutation in intron 2 of the ITPA gene.

5. The method of claim 1, said method further comprising:
   correlating the genotype of said subject with a level of inosine triphosphate pyrophosphatase (ITPase) activity.

6. A method for optimizing therapeutic efficacy in a human subject having Crohn's disease or ulcerative colitis and receiving azathioprine (AZA) or 6-mercaptopurine (6-MP), said method comprising:
   (a) genotyping nucleic acid in a sample from said subject for the presence of a 94 C to A mutation in the inosine triphosphate pyrophosphatase (ITPA) coding region;
   (b) predicting the presence of said mutation indicates an increased risk of flu-like symptoms relative to a subject without said mutation and predicting the presence of said mutation does not indicate an increased risk of myelosuppression relative to a subject without said mutation; and
   (c) optimizing therapeutic efficacy by administering an alternative therapeutic agent to a subject to avoid flu-like symptoms.

7. The method of claim 6, wherein said alternative therapeutic agent is selected from the group consisting of an anti-inflammatory agent, an immunosuppressive agent, and combinations thereof.

8. The method of claim 6, wherein said alternative therapeutic agent is 6-thioguanine or a derivative thereof.

9. The method of claim 6, wherein said alternative therapeutic agent is a lower dose of AZA or 6-MP.

10. The method of claim 6, said method further comprising:
    correlating the genotype of said subject with a level of inosine triphosphate pyrophosphatase (ITPase) activity.

11. The method of claim 1, wherein said nucleic acid comprises genomic DNA.

12. The method of claim 1, wherein said nucleic acid is genotyped using the polymerase chain reaction.

13. The method of claim 1, wherein said sample is selected from the group consisting of whole blood, plasma, and serum.

14. The method of claim 6, wherein said nucleic acid comprises genomic DNA.

15. The method of claim 6, wherein said nucleic acid is genotyped using the polymerase chain reaction.

16. The method of claim 6, wherein said sample is selected from the group consisting of whole blood, plasma, and serum.

17. The method of claim 6, wherein said subject is heterozygous for said 94 C to A mutation.

18. The method of claim 6, wherein said subject is homozygous for said 94 C to A mutation.

19. The method of claim 6, wherein said subject is compound heterozygous for said 94 C to A mutation and a 21 A to C mutation in intron 2 of the ITPA gene.

* * * * *